United States Patent [19]
Lillerud et al.

[11] Patent Number: 6,001,328
[45] Date of Patent: Dec. 14, 1999

[54] CRYSTALLINE METALLOPHOSPHATES

[75] Inventors: Karl Petter Lillerud; Erling N. Halvorsen; Arne Karlsson; Duncan Akporiaye, all of Oslo; Jorun Hustveit, Sauda, all of Norway

[73] Assignee: Norsk Hydro ASA, Oslo, Nauru

[21] Appl. No.: 09/142,498

[22] PCT Filed: Mar. 13, 1997

[86] PCT No.: PCT/NO97/00076

§ 371 Date: Apr. 14, 1999

§ 102(e) Date: Apr. 14, 1999

[87] PCT Pub. No.: WO97/33693

PCT Pub. Date: Sep. 18, 1997

[30]     Foreign Application Priority Data

Mar. 13, 1996  [NO]  Norway ..................................... 961033

[51] Int. Cl.$^6$ .......................... C01B 37/08; C01B 25/36; C01B 25/45; B01J 29/83; B01J 29/85
[52] U.S. Cl. ......................... 423/718; 423/705; 423/707; 423/305; 423/306; 423/DIG. 30; 502/208; 502/214; 585/640
[58] Field of Search ..................... 423/705, 718, 423/707, DIG. 30, 305, 306; 502/208, 214; 585/640

[56]             References Cited

U.S. PATENT DOCUMENTS

| | | | |
|---|---|---|---|
| 4,310,440 | 1/1982 | Wilson et al. ........................... | 502/208 |
| 4,418,048 | 11/1983 | Dyer et al. ............................. | 423/305 |
| 4,440,871 | 4/1984 | Lok et al. ............................... | 502/214 |
| 4,639,357 | 1/1987 | Derouane et al. ................. | 423/DIG. 30 |
| 4,666,692 | 5/1987 | Taramasso et al. ..................... | 423/718 |
| 4,793,984 | 12/1988 | Lok et al. ........................ | 423/DIG. 30 |
| 5,035,870 | 7/1991 | Clark et al. . | |
| 5,096,684 | 3/1992 | Guth et al. .............................. | 423/306 |

OTHER PUBLICATIONS

Chemical Abstracts 114:34650z (1991), "Fluorine–19 MAS NMR studies of crystalline microporous solids synthesized in the fluoride medium", Delmotte et al., Zeolites 1990, 10(8), 778–83 (No Month).

Chemical Abstracts 121:259057f(1994), "Synthesis of new microporous AlPO$_4$ and substituted derivatives with the LTA structure", Sierea et al., Microporous Mater. 1994, 3(1–2), 29–38 (No Month).

*Primary Examiner*—Mark L. Bell
*Assistant Examiner*—David Sample
*Attorney, Agent, or Firm*—Wenderoth, Lind & Ponack, L.L.P.

[57]                ABSTRACT

Microporous crystalline metallophosphate composition having an essential framework structure whose chemical composition in the as synthesised form expressed in terms of mole rations of oxides is: $mR(M_xAl_yP_z)O_2$ where M is silicon, $x+y+z=1$, m may have a value from 0.02 to 0.3, R is at least one templating agent, x, y and z represent the mole fractions of silicon, aluminium and phosphorous presentin the product, and where x may have a value from 0 to 0.5, y may have a value from 0.25 to 0.5 and z may have a value from 0.25 to 0.5, and where one reactive form of fluoride may be present in an effective amount to form the product, and having a characteristic X-ray powder diffraction pattern containing at least the d-spacings as set forth in Table 1.

8 Claims, No Drawings

CRYSTALLINE METALLOPHOSPHATES

The present invention relates in general to a crystalline metallophosphates, and more particularly to crystalline aluminophosphates and silicoaluminophosphates of the molecular sieve type with a novel structure and the method for its preparation.

Microporous crystalline aluminophosphate compositions having open framework structures formed of $AlO_2$ and $PO_2$ tetrahedral units joined by the sharing of the corner oxygen atoms and characterised by having pore openings of uniform dimensions have heretofore been disclosed in a number of publications. U.S. Pat. No. 4,310,440 describes aluminophosphates which constitute a generic class of non-zeolite molecular sieve materials being capable of undergoing complete and reversible dehydration while retaining the same essential framework topology in both the anhydrous and hydrated state.

Microporous crystalline silicoaluminophosphate compositions having open framework structures formed of $AlO_2$, $PO_2$ and $SiO_2$ tetrahedral units joined by sharing of corner oxygen atoms and characterised by having pore openings of uniform dimension is earlier disclosed for example in U.S. Pat. No. 4,440,871. These products have a chemical composition on a water-free basis as follows:

$$mR:(Si_xAl_yP_z)O_2$$

where "R" represents at least one organic template material which is present in the intracrystalline pore system; "m" is the number of moles of "R" present per mole of $(Si_xAl_yP_z)O_2$ and m has a value between 0 and 0.3, the maximum value in each case being dependent on the molecular dimensions of the template material and the available pore volume in the silico-alumino-phosphate structure in question; "x", "y" and "z" are molar fractions of silicon, aluminium and phosphorus respectively, present as tetrahedral oxides. The minimum value of "x", "y" and "z" is 0.01, and the maximum value of "x" is 0.98, of "y" 0.6 and of "z" 0.52. The minimum value of "m" in the formula above is 0.02.

Also the silicoaluminophosphates constitute a generic class of non-zeolite molecular sieve materials being capable of undergoing complete and reversible dehydration while retaining the same essential framework topology in both the anhydrous and hydrated state.

By the term "essential framework topology" or "essential framework structure" as used in the aforesaid patents, and also in the present specification and claims, is meant the spatial arrangement of the primary Al—O, Si—O and P—O bond linkages.

From U.S. Pat. No. 5,370,851 there is also known silico-alumino-phosphate molecular sieves of the same composition, but with different X-ray diffraction pattern. Chlorides are used in the synthesis.

WO93/13013 describes synthesis of silico-aluminophosphates with improved stability to activation and with a controlled silicon content. Hydrochloric acid is used in the synthesis.

Other microporous aluminophosphates which undergo structure rearrangements, either reversibly or irreversibly, upon partial or complete dehydration are also known, for example the minerals variscite and metavaricite and certain of the synthetic metastable aluminophosphates reported by F. D'Yvoire [Bull.Soc.Chim. France, 1762 (1961)].

Synthesis of microporous crystalline silicoaluminophosphates where the reaction mixture is modified with fluoride ions, is earlier described for example in U.S. Pat. No. 4,786,487.

The present invention concerns a novel microporous crystalline metalloophosphate composition, and the method for its preparation.

The microporous crystalline metallophosphate composition has an essential framework structure whose chemical composition in the as synthesised form expressed in terms of mole ratios of oxides is:

$$mR(M_xAl_yP_z)O_2$$

where M is silicon, $x+y+z=1$, m may have a value from 0.02 to 0.3, R is at least one templating agent, x, y and z represent the mole fractions of silicon, aluminium and phosphorous present in the product, and where x may have a value from 0 to 0.5, y may have a value from 0.25 to 0.5 and z may have a value from 0.25 to 0.5, and where one reactive form of fluoride may be present in an effective amount to form the product, and having a characteristic X-ray powder diffraction pattern containing at least the d-spacings as set forth hereinafter in Table I.

The product can have a chemical composition, expressed in terms of mole ratios of oxides, (taken from Example 1):

$$0.17\ SiO_2:Al_2O_3:0.81\ P_2O_5$$

and exhibits and X-ray powder diffraction pattern, in its as synthesised form, which contains at least the d-spacings set forth in Table I set forth hereinafter. The chemical composition can be altered from the one mentioned above, by for instance altering the chemical composition of the reaction mixture.

The metallophosphate can be prepared by hydrothermal crystallisation from a reaction mixture prepared by combining reactive sources of phosphorus, silicon and aluminium with water and fluoride and at least one structure directing agent (template) which can include organic amines and quartenary ammonium compounds, and most preferably tetramethylammonium hydroxide. In the as-synthesized form, wherein the product prepared by hydrothermal crystallisation has not been subjected to a post-synthesis treatment effective in removing the structure directing agent, this agent is contained within the framework structure of the metallophosphate in the amounts which vary per mole of $Al_2O_3$. The structure directing agent is readily removed by calcination and does not appear to be an essential constituent of the product.

The novel microporous metallophosphate of the present invention can be produced by hydrothermal crystallisation from a reacting mixture containing reactive sources of phosphorous, silicon, fluorine and aluminium and a organic templating agent, preferably tetramethylammonium hydroxide. The preparative process typically comprises forming a reaction mixture which in terms of molar ratios of oxides is $$0-4\ SiO_2:Al_2O_3:0.5-6\ P_2O_5:7-300\ H_2O$$

and contains at least one organic templating agent and one reactive form of fluorine in an effective amount which forms the product. Representative of the amount of organic template employed herein is an amount between 0.5 and about 5 moles of organic templating agent, and 0.01 to 3 moles of HF per mole of $Al_2O_3$. The reaction mixture is placed in a reaction vessel inert towards the reaction mixture and heated to a temperature of at least about 70° C., preferably between 75° C. and 200° C., until crystallised, usually for a period from 2 hours to 3 weeks or more. The solid crystalline reaction product is then recovered by any convenient method, such as filtration or centrifugation, washed with water and dried in air at a temperature between ambient and about 110° C.

In a preferred crystallisation method, a solution is prepared from hydrated alumina, aqueous solution of phosphoric acid, colloidal silica, hydrofluoric acid, and an organic templating agent and is then heated to about 150° C. from 1 day to 2 weeks. The preferred ratio of inorganic oxides in the initial solution is:

0.05–0.5 $SiO_2$:$Al_2O_3$:0.5–4 $P_2O_5$:20–200 $H_2O$

The preferred initial solution contains between 0.5 and 2.5 moles of organic templating agent and 0.1 to 2 moles of HF per mole of $Al_2O_3$.

The material of present invention can alternatively be crystallised from a gel formed from an organic templating agent and appropriate phosphorous, silicon, fluorine and aluminium sources such as phosphoric acid, Ludox LS, hydrofluoric acid and pseudo-boehmite hydrated aluminium oxide, and digested via conditions typical of those detailed in U.S. Pat. No. 4,440,871.

Not all templating agents suitably employed in preparation of all silicoaluminophosphates are believed to be generally suitable for the preparation of the product. The use of tetramethylammonium hydroxide has been found to act as an acceptable templating agent for use in the preparation.

The as-synthesized compositions are isolated after synthesis and advantageously washed with water. The as-synthesized compositions may contain the organic templating agent within the intracrystalline pore system. The form of the organic templating agent may be an occluded molecular species (or may be present as a charge balancing cation). The fluoride may also be present in the structure and may be engaged in mutual interaction with the template or with the framework as a stabilising unit, it may also be present as an occluded species. In general, it is desirable to remove the organic templating agent by for example calcination at a temperature sufficient to remove substantially all of the organic templating agent. The calcination temperature is generally between 300° C. and about 700° C., i.e., whereby the organic templating agent is removed by thermal degradation.

The template-containing as-synthesized form of the silicoaluminophosphate of the present invention has an essential framework structure whose chemical composition expressed in terms of mole ratios of oxides can be (taken from Example 1):

0.17 $SiO_2$:$Al_2O_3$:0.81 $P_2O_5$ and has characteristic X-ray powder diffraction pattern which contains at least the d-spacings set forth in Table I below:

TABLE I

| 2 θ | d (Å) | Relative Intensity |
|---|---|---|
| 10.4–10.7 | 8.50–8.26 | VS |
| 11.3–11.7 | 7.82–7.56 | W |
| 12.0–12.3 | 7.37–7.19 | W |
| 13.2–13.6 | 6.70–6.51 | W |
| 19.6–20.0 | 4.53–4.44 | M |
| 20.7–21.1 | 4.29–4.21 | M |
| 23.0–23.4 | 3.86–3.80 | M |
| 23.6–24.0 | 3.77–3.70 | W |
| 24.4–24.7 | 3.65–3.60 | W |
| 25.4–25.8 | 3.50–3.45 | W |
| 27.1–27.5 | 3.29–3.24 | W |

In some of the X-ray patterns reported, the relative intensities of the d-spacings are indicated by the notations VS, S, M, W and VW which represents Very Strong, Strong, Medium, Weak and Very Weak, respectively.

The above X-ray pattern and all other X-ray patterns appearing hereinafter were obtained by use of either a standard X-ray powder diffraction technique or by use of computer based techniques using a Siemens D-500 X-ray powder diffractometer. When the standard X-ray technique is employed the radiation source is a high-intensity, copper target, X-ray tube operated at 40 kV and 50 mA. The diffraction pattern from the copper K-alpha radiation and Germanium monochromator were recorded by a X-ray spectrometer scintillation counter, pulse height analyser and strip chart recorder.

Flat compressed powder samples are scanned at 1 degrees (2θ) per minute. Interplanar spacings (d) in the Angstrom units are obtained from the position of the diffraction peaks as 2θ where theta is the Bragg angle. Intensities were determined from the heights of diffraction peaks after subtracting background, "$I_0$" being the intensity of the strongest line or peak, and "I" being the intensity of each of the other peaks.

As will be understood by those skilled in the art, the parameter 2θ, irrespective of the technique employed, is subjected to both human and mechanical error, which in combination, can impose an uncertainty of about 0.4° on each reported value of 2 theta. This uncertainty is of course, also manifested in the reported value of the d-spacings, which are calculated from the 2 theta values. This imprecision is general throughout the art and is not sufficient to preclude the differentiation of the present crystalline materials from the compositions of the prior art. The relative intensities and peak positions may vary with the hydration state of the samples, and the content of organic and inorganic material. Further the relative intensities may also vary due to for example orientational effects of the crystals.

When the as-synthesized compositions are calcined, i.e., heated to a temperature sufficiently high (typically in the 300° C. to 700° C. range) or otherwise treated, such as by chemical oxidation, to remove essentially all of the organic templating agent present in the intracrystalline pore system and are allowed to rehydrate in ambient air, the composition has an X-ray powder diffraction pattern which contains at least the d-spacings set forth in Table II below:

TABLE II

| 2 θ | d (Å) | Relative Intensity |
|---|---|---|
| 10.40 | 8.50 | VS |
| 12.05 | 7.34 | W |
| 12.49 | 7.08 | W |
| 13.11 | 6.75 | W |
| 13.83 | 6.40 | W |
| 20.83 | 4.29 | M |
| 24.05 | 3.69 | W |

The product exhibits surface characteristics which make it useful as a catalyst or catalyst support in various hydrocarbon conversion and oxidative combustion processes. The product can be associated with catalytically active metals, e.g., by framework substitution, by impregnation, doping and the like, by methods traditionally used in the art for fabrication of catalyst compositions.

Among the hydrocarbon conversion reactions that can be catalysed by the new composition are cracking, hydrocracking, alkylation for both the aromatic and isoparaffin types, isomerization including xylene isomerization, polymerisation, reforming, hydrogenation, dehydrogenation, transalkylation, dealkylation, hydrodecyclization and dehydrocyclization.

The results further show that the new compositions have a narrow pored structure with a pore size of at less than 4

Angstrom, which make them suitable for use as methanol to olefin catalysts.

The following examples are provided to illustrate the invention and are not to be construed as limiting thereof:

EXAMPLE 1 a) A reaction mixture was prepared by combining 3.39 grams of a pseudo-boehmite phase (73.2 wt. % $Al_2O$) and 15.87 grams $H_2O$ to which was added 5.52 grams of 85 wt. % orthophosphoric acid ($H_3PO_4$), and stirred until homogeneous. 0.5 grams of Ludox LS (approx. 30 wt. % $SiO_2$) and 0.53 grams of 48 wt. % hydrofluoric acid (HF) was blended into this mixture. To this mixture was added 4.28 grams of tetramethylammonium hydroxide pentahydrate (TMA) and stirred until homogeneous. The composition of the final mixture, in terms of molar oxide ratios was:

1.0 TMA:0.1 $SiO_2$:$Al_2O_3$:$P_2O_5$:0.5 HF:50 $H_2O$

The reaction mixture (30 grams) was sealed in a Teflon jar and heated in an oven at 150° C. for 21 hours. The solids were recovered by centrifugation, washed with $H_2O$, and dried in air at ambient temperature.

The 3.7 grams of dried product had an X-ray powder diffraction pattern which indicated the product with a smaller amount of an impurity phase. The product had an X-ray powder diffraction pattern characterised by the data in Table A.

TABLE A

| 2 θ | d (Å) | 100 I/Io |
|---|---|---|
| 10.61 | 8.33 | 100 |
| 11.49 | 7.69 | 2 |
| 12.51 | 7.28 | 5 |
| 13.46 | 6.57 | 8 |
| 14.47 | 6.11 | 1 |
| 17.16 | 5.16 | 1 |
| 18.07 | 4.91 | 1 |
| 19.80 | 4.48 | 13 |
| 20.90 | 4.25 | 24 |
| 21.88 | 4.06 | 1 |
| 23.20 | 3.83 | 12 |
| 23.81 | 3.73 | 5 |
| 24.59 | 3.62 | 10 |
| 25.62 | 3.47 | 8 |
| 27.30 | 3.26 | 3 |
| 28.21 | 3.16 | 1 |
| 29.17 | 3.06 | 1 | b) A portion of the product obtained in part a) was calcined in air by heating to 600° C. and holding at 600° C. for 4.5 hours. After cooling to room temperature and rehydrating in ambient air, the calcined solid had a X-ray powder diffraction pattern characterised by the data in the following table:

TABLE B

| 2 θ | d (Å) | 100 I/I$_o$ |
|---|---|---|
| 10.40 | 8.49 | 100 |
| 12.05 | 7.34 | 2 |
| 12.49 | 7.08 | 2 |
| 13.10 | 6.75 | 4 |
| 13.83 | 6.36 | 4 |
| 14.73 | 6.01 | 1 |
| 15.85 | 5.59 | 3 |
| 19.57 | 4.53 | 4 |
| 20.11 | 4.41 | 5 |
| 20.68 | 4.29 | 10 |

TABLE B-continued

| 2 θ | d (Å) | 100 I/I$_o$ |
|---|---|---|
| 21.86 | 4.06 | 5 |
| 22.32 | 3.98 | 2 |
| 23.16 | 3.83 | 5 |
| 24.05 | 3.69 | 10 |
| 24.64 | 3.61 | 3 |
| 26.11 | 3.41 | 9 |
| 26.92 | 3.31 | 3 |
| 27.69 | 3.22 | 3 |
| 29.32 | 3.04 | 2 |

A portion of the 3.7 grams of calcined product was analysed and the following chemical analysis obtained:

0.17 $SiO_2$:$Al_2O_3$:0.81 $P_2O_5$

EXAMPLE 2

A reaction mixture was prepared by combining 3.28 grams of a pseudo-boehmite phase (73.2 wt. % $Al_2O_3$) and 15.45 grams $H_2O$ to which was added 5.49 grams of 85 wt. % orthophosphoric acid ($H_3PO_4$), and stirred until homogeneous. 0.52 grams of Ludox LS (approx. 30 wt % $SiO_2$) and 1.0 grams of 48 wt. % hydrofluoric acid (HF) was blended into this mixture. To this mixture was added 4.33 grams of tetramethylammonium hydroxide pentahydrate (TMA) and stirred until homogeneous. The composition of the final mixture, in terms of molar oxide ratios was:

1.0 TMA:$Al_2O_3$:$P_2O_5$:1HF:0.1 $SiO_2$:50 $H_2O$

The reaction mixture (approx. 30 grams) was sealed in a Teflon jar and heated in an oven at 150° C. for 21 hours. The solids were recovered by centrifugation, washed with $H_2O$, and dried in air at ambient temperature.

The approx. 3 grams of dried product had an X-ray powder diffraction pattern which indicated UiO-S7 with a smaller amount of an impurity phase. The product had an X-ray powder diffraction pattern characterised by the data in Table A.

EXAMPLE 3

A fluoride modified aluminophosphate gel containing the organic amine tetramethyl ammonium hydroxide (TMAOH) was prepared. The gel had a molar oxide ratio of 1 $Al_2O_3$:1 $P_2O_5$:0.2 HF:1 TMAOH:$H_2O$ The gel was prepared in teflon liners in which pseudobohemite was first mixed with water and phosphoric acid. The amine was then added followed by HF after which the gel was well stirred. The liners were put in stainless steel autoclaves and heated in an oven at 150° C. for 21 hours, after which they were quenched in cold water and the microcrystalline product separated, washed with water and dried. The product had an X-ray powder diffraction pattern characterised by the data in Table I.

We claim:

1. Microporous crystalline metallophosphate composition having an essential framework structure whose chemical composition in the as synthesised form expressed in terms of mole ratios of oxides is:

mR($M_xAl_yP_z$)$O_2$ where M is silicon, x+y+z=1, m is from 0.02 to 0.3, R is at least one templating agent, x, y and z represent the mole fractions of silicon, aluminium and phosphorous present in the product, and where x is from 0 to 0.5, y may have a value from 0.25 to 0.5 and z is from 0.25 to 0.5, and where one reactive form of fluoride may be present in an effective amount to form the product, and having a characteristic X-ray powder diffraction pattern containing at least the d-spacings and relative intensities as set forth below:

| d (Å) | Relative Intensity |
|---|---|
| 8.50–8.26 | VS |
| 7.82–7.56 | W |
| 7.37–7.19 | W |
| 6.70–6.51 | W |
| 4.53–4.44 | M |
| 4.29–4.21 | M |
| 3.86–3.80 | M |
| 3.77–3.70 | W |
| 3.65–3.60 | W |
| 3.50–3.45 | W |
| 3.29–3.24 | W. |

2. A calcined silicoaluminophosphate, having a characteristic X-ray powder diffraction pattern comprising at least the d-spacings and relative intensities as set forth below

| d (Å) | Relative Intensity |
|---|---|
| 8.50 | VS |
| 7.34 | W |
| 7.08 | W |
| 6.75 | W |
| 6.40 | W |
| 4.29 | M |
| 3.69 | W |

3. A calcined silicoaluminophosphate according to claim 2, wherein the chemical compositions in terms of mole ratios of oxides is:

$$0.17\ SiO_2:Al_2O_3:0.81\ P_2O_5$$

and having a characteristic X-ray powder diffraction pattern comprising at least the d-spacings and relative intensities as set forth below:

| d (Å) | Relative Intensity |
|---|---|
| 8.49 | 100 |
| 7.34 | 2 |
| 7.08 | 2 |
| 6.75 | 4 |
| 6.36 | 4 |
| 6.01 | 1 |
| 5.59 | 3 |
| 4.53 | 4 |
| 4.41 | 5 |
| 4.29 | 10 |
| 4.06 | 5 |
| 3.98 | 2 |
| 3.83 | 5 |
| 3.69 | 10 |
| 3.61 | 3 |
| 3.41 | 9 |
| 3.31 | 3 |
| 3.22 | 3 |
| 3.04 | 2 |

4. Process for preparing a microporous crystalline silicoaluminophosphate composition according to any one of claims 1–3, wherein a reaction mixture is formed having a composition in terms of mole ratios of oxides of $$0\text{--}4\ SiO_2:Al_2O_3:0.5\text{--}6\ P_2O_5:7\text{--}300\ H_2O$$

and containing from 0.5 to about 5 moles of at least one organic templating agent, and containing from 0.01 to about 3 moles of a reactive fluorine source, and heating the reaction mixture thus formed at a temperature of at least 70° C. to about 200° C. under autogenous pressure until crystals of said metallophosphate are formed.

5. Process according to claim 4, wherein a reaction mixture is formed having a composition in terms of mole ratios of oxides of $$0.05\text{--}0.5\ SiO_2:Al_2O_3:0.5\text{--}4\ P_2O_5:20\text{--}200\ H_2O.$$

6. Process according to claim 4, wherein tetramethylammonium hydroxide is used as templating agent.

7. Process according to claim 4, wherein there is used a gel composition in terms of molar ratios as follows:

$$1.0\ TMA:0.1\ SiO_2:Al_2O_3:P_2O_5:0.5\ HF:50\ H_2O.$$

8. A method of producing olefins from methanol comprising contacting methanol with a catalyst comprising the composition of any one of claims 1–3 under conditions effective to form olefins.

* * * * *